| United States Patent [19] | [11] | 4,271,125 |
|---|---|---|
| Leichnitz | [45] | Jun. 2, 1981 |

[54] INDICATOR DEVICE FOR THE QUANTITATIVE DETERMINATION OF METAL CYANIDES IN AEROSOL FORM

[75] Inventor: Kurt Leichnitz, Gross Grönau, Fed. Rep. of Germany

[73] Assignee: Drägerwerk Aktiengesellschaft, Fed. Rep. of Germany

[21] Appl. No.: 93,874

[22] Filed: Nov. 13, 1979

[30] Foreign Application Priority Data

Dec. 16, 1978 [DE] Fed. Rep. of Germany ....... 2854421

[51] Int. Cl.$^3$ ............................................. G01N 31/22
[52] U.S. Cl. ................................ 422/86; 23/232 R; 422/60; 252/408
[58] Field of Search .................................. 422/55–61, 422/84–86; 23/232 R; 252/408

[56] References Cited

U.S. PATENT DOCUMENTS 3,223,487  12/1965  Grosskoff ............................... 422/86

FOREIGN PATENT DOCUMENTS 1143818  2/1969  United Kingdom ....................... 422/84

OTHER PUBLICATIONS

Testing Tube Pocketbook, Dragerwerk AG, Reprint 2340, p. 46, 5-1976.
Gen. Chemistry; L. Pauling; 1958, p. 382, 2nd ed.

*Primary Examiner*—Michael S. Marcus
*Attorney, Agent, or Firm*—McGlew and Tuttle

[57] ABSTRACT

An indicator device for the quantitative determination of aerosol-type metal cyanides, including a tube provided with a bore extending therethrough, a front layer of a substrate material impregnated with sulfuric acid or phosphoric acid and a following indicating layer of a substrate impregnated with mercuric chloride and methyl red.

8 Claims, 1 Drawing Figure

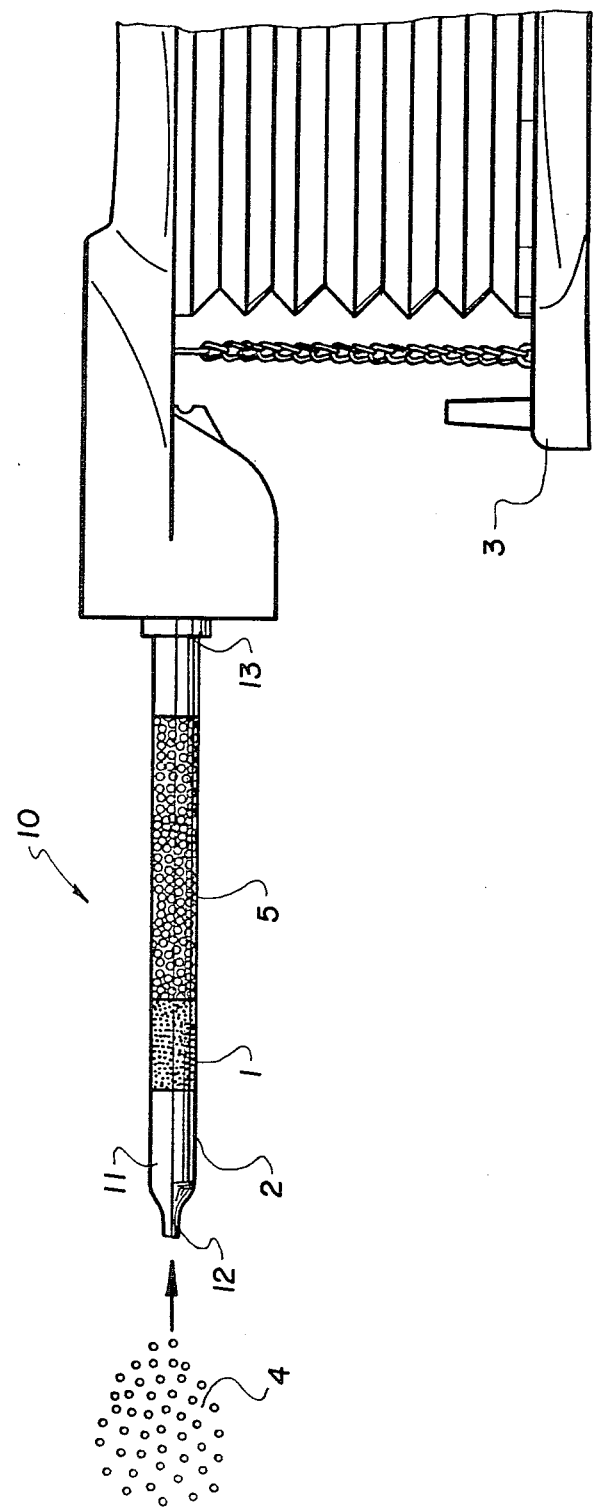

INDICATOR DEVICE FOR THE QUANTITATIVE DETERMINATION OF METAL CYANIDES IN AEROSOL FORM

FIELD AND BACKGROUND OF THE INVENTION

This invention relates to gas testing devices in general and, more particularly, to a new and useful indicator device for the quantitative determination of metal cyanides in aerosol form.

Indicator tubes for the quantitative determination of aerosol-type metal cyanides have not yet been known heretofore. The reason for this lies in the unclear reaction behavior of the aerosols with the indicating preparations of the indicator tubes.

A known method for detecting both volatile and misty arsines uses an indicator tube in which a filter of inorganic or organic silica gel, e.g., glass wadding, cellulose, asbestos, is arranged in front of a highly active silica gel layer. When an air sample is passed therethrough, the arsine mists contained in the sample are retained by the filter and volatile arsines are fixed by the silica gel. Subsequently, a reagent in the form of a solution of tin chloride in concentrated hydrochloric acid is introduced into the indicator tube.

The mist particles retained by the filter are entrained by the reagent and flushed to the silica gel layer. They react with the reagent only on the silica gel. The reaction in the form of an arsenic deposit is always observed in the silica gel layer on the silica gel, regardless of whether arsine mists or volatile compounds are present. The reaction takes place directly between the substances to be detected and the indicating reagent. This measuring method therefore permits only a qualitative determination of the arsines. In addition, the use of the liquid reaction solution is not entirely harmless (see German Patent No. 742,689).

In a known indicator tube for the determination of hydrogen cyanide, mercuric chloride and methyl red are used as a reagent system. However, this reagent system only reacts with hydrogen cyanide, and not with metal cyanides ("Testing Tube Pocketbook", Drägerwerk AG, Reprint 2340, May 1976, pp. 82–83).

SUMMARY OF THE INVENTION

The problem underlying the invention is to provide an indicator tube with quantitative indication for the determination of aerosol metal cyanides.

In accordance with the invention, the indicator tube comprises, in the direction of flow of the gas to be measured, a known glass tube having a gas permeable front layer and a following indicating layer. According to the simple solution of the invention, the front layer is impregnated with sulfuric acid or phosphoric acid. The metal cyanides in aerosol form are completely deposited in the front layer due to sorption onto the material of the front layer. Thereafter, the metal cyanides react quantitatively with the acid in the front layer to form the readily volatile compound hydrogen cyanide. In a stoichiometric view of the reaction, the acid present exceeds the relative amount of the metal cyanides. The amount of the readily volatile hydrogen cyanide formed in the front layer is proportional to the reacted amount of the aerosol type metal cyanides deposited in the front layer. The readily volatile hydrogen cyanide flows to the rear indicating layer where it is measured, in a known manner, by a color reaction.

This simple indicator tube, which has only two layers, ensures a reliable quantitative determination of the existing aerosol metal cyanides.

Accordingly, it is an object of the invention to provide an indicator device for the quantitative deteremination of metal cyanides in aerosol form including a tube having a bore extending therethrough from an entrance end for receiving metal cyanides to an exit end, gas permeable means within said bore adjacent said entrance end, said gas permeable means including a carrier member and an acid impregnated in said carrier member selected from the group consisting of sulfuric acid and phosphoric acid, and indicating means within said bore intermediate said gas permeable means and said exit end, said indicator means having a carrier member impregnated with mercuric chloride and methyl red.

A further object of the invention is to provide an indicator device for the quantitative determination of metal cyanides in aerosol form which is simple in design, rugged in construction and economical to manufacture. The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

The sole FIGURE of the drawing is a schematic representation of an indicator device constructed in accordance with the present invention.

DESCRIPTION OF THE PREFERRED EMBODIMENT

Referring to the drawing in particular, the invention embodied therein, comprises, an indicator tube, generally designated 10, for the quantitative determination of metal cyanides in aerosol form.

The indicator tube contains a front layer 1, in a glass tube 2, and a following indicating layer 5 in the direction of flow of the gas to be measured. The gas sample 4 to be measured, containing an aerosol-type metal cyanide, is drawn by a pump 3 through a bore 11 of the glass tube which extends from an entrance end 12 that is open after points have been broken off to an exit end 13 connected to the pump. The gas-permeable front layer 1 acts as a filter for the aerosol and includes a substrate or carrier material, for example, silica gel, glass fibers or the like, which is impregnated with sulfuric acid or phosphoric acid. The aerosol-type metal cyanide contained in the gas sample 4 reacts with, for example, the sulfuric acid, after it has been deposited on front layer 1 to form hydrogen cyanide, according to the general equation:

$$\text{Metal Cyanide} + H_2SO_4 \rightarrow HCN + \text{Metal Sulfate}$$

The hydrogen cyanide, in the form of a gaseous reaction product then reacts in the following indicating layer 5 with the reagent mercuric chloride, which is already known for use in indicator tubes, according to the formula:

$$HCN + HgCl_2 \rightarrow HCl$$

to form hydrogen chloride, which, in turn, with methyl red, yields a red color in indicating layer 5. The amount of the reaction product is then measured.

While a specific embodiment of the invention has been shown and described in detail to illustrate the application of the principles of the invention, it will be understood that the invention may be embodied otherwise without departing from such principles.

What is claimed is:

1. An indicator device for the quantitative determination of metal cyanides in aerosol form, comprising, a tube having a bore extending therethrough from an entrance end for receiving the metal cyanides to an exit end, gas-permeable means within said bore adjacent said entrance end, said gas-permeable means including a carrier member and an acid impregnated in said carrier member, and indicating means within said bore intermediate said gas-permeable means and said exit end, said indicator means having a carrier member impregnated with mercuric chloride and methyl red.

2. The device according to claim 1, wherein said acid is sulfuric acid.

3. The device according to claim 1, wherein said acid is phosphoric acid.

4. The device according to claim 1, further comprising, pump means connected to said exit end for drawing the metal cyanides through said bore.

5. The device according to claim 1, wherein the quantity of acid exceeds the relative amount of metal cyanides on a stoichiometric basis.

6. The device according to claim 1, wherein said gas-permeable means comprises a first layer in said bore and said indicating means comprises a second layer in said bore, and said tube includes only said first layer and said second layer in said base.

7. The device according to claim 1, wherein said bore of said tube is closed at said entrance end and further comprising means for opening said entrance end.

8. The device according to claim 7, wherein said tube is glass and said opening means includes a tip which may be readily broken away.

* * * * *